United States Patent [19]

Parsons et al.

[11] Patent Number: 5,171,281

[45] Date of Patent: Dec. 15, 1992

[54] FUNCTIONAL AND BIOCOMPATIBLE INTERVERTEBRAL DISC SPACER CONTAINING ELASTOMERIC MATERIAL OF VARYING HARDNESS

[75] Inventors: John R. Parsons, Perth Amboy; Casey K. Lee, Short Hills; Noshir A. Langrana, Robbinsville; Alastair J. Clemow, Princeton; Elizabeth H. Chen, Princeton, all of N.J.

[73] Assignees: University of Medicine & Dentistry of New Jersey, Newark; Rutgers University, Piscataway, both of N.J.

[21] Appl. No.: 776,708

[22] Filed: Oct. 9, 1991

Related U.S. Application Data

[63] Continuation of Ser. No. 382,207, Jul. 24, 1989, abandoned, which is a continuation-in-part of Ser. No. 233,617, Aug. 18, 1988, abandoned.

[51] Int. Cl.⁵ .................................................. A61F 2/44
[52] U.S. Cl. .................................................. 623/17
[58] Field of Search ........................................ 623/17

[56] References Cited

U.S. PATENT DOCUMENTS

| | | |
|---|---|---|
| 3,503,199 | 3/1970 | Nesbitt-Dufort . |
| 3,593,342 | 7/1971 | Niebauer et al. . |
| 3,683,422 | 8/1972 | Stemmer et al. . |
| 3,867,728 | 2/1975 | Stubstad et al. ............... 623/17 |
| 4,146,936 | 4/1979 | Aoyagi et al. . |
| 4,202,055 | 5/1980 | Reiner et al. . |
| 4,222,128 | 9/1980 | Tomonaga et al. . |
| 4,309,777 | 1/1982 | Patil . |
| 4,313,232 | 2/1982 | Habal et al. . |
| 4,314,380 | 2/1982 | Miyata et al. . |
| 4,349,921 | 9/1982 | Kuntz . |
| 4,356,571 | 11/1982 | Esper et al. . |
| 4,366,183 | 12/1982 | Ghommidh et al. . |
| 4,454,612 | 6/1984 | McDaniel et al. . |
| 4,512,038 | 4/1985 | Alexander et al. . |
| 4,576,608 | 3/1986 | Homsy . |
| 4,599,085 | 7/1986 | Riess et al. . |
| 4,636,217 | 1/1987 | Ogilvie et al. . |
| 4,655,777 | 4/1987 | Dunn et al. . |
| 4,662,888 | 5/1987 | Field . |
| 4,711,286 | 12/1987 | Kabe et al. . |
| 4,714,467 | 12/1987 | Lechner et al. . |
| 4,911,718 | 3/1990 | Lee et al. . |
| 4,932,969 | 6/1990 | Frey et al. ...................... 623/17 |

FOREIGN PATENT DOCUMENTS

0030583  12/1979  European Pat. Off. .

OTHER PUBLICATIONS

J. Biomed. Mat. Res. Symposium No. 4, pp. 165-186 (1973)(Urbaniak et al.) Product Literature Link Intervertebral Endoprosthesis SB Charite.

Primary Examiner—David Isabella
Assistant Examiner—Debra S. Brittingham
Attorney, Agent, or Firm—Klauber & Jackson

[57] ABSTRACT

The construction and manufacturing technique for a functional biocompatible intervertebral disc spacer is described. This device is useful for a replacement for a degenerated disc in certain treatments of back pain and spinal disease. The disc spacer possesses mechanical properties skin to those of the normal disc and will preserve normal functions of the spinal motion segment. The device achieves the desired properties by varying the hardness of the elastomeric material in its nucleus and annulus.

28 Claims, 2 Drawing Sheets

FUNCTIONAL AND BIOCOMPATIBLE INTERVERTEBRAL DISC SPACER CONTAINING ELASTOMERIC MATERIAL OF VARYING HARDNESS

BACKGROUND OF THE INVENTION

This application is a continuation of U.S. application Ser. No. 382,207 filed on Jul. 24, 1989 now abandoned, which is a continuation-in-part of co-pending application Ser. No. 07/233,617, filed Aug. 18, 1988 priority of which is claimed hereunder now abandoned.

The intervertebral disc is a complex joint anatomically and functionally. It is composed of three component structures: the nucleus pulposus, the annulus fibrosus and the vertebral endplates. The biomedical composition and anatomical arrangements within these component structures are related to the biomechanical function of the disc.

The nucleus pulposus occupies 25-40 percent of the total disc cross-sectional area. It is composed mainly of mucoid material containing mainly proteoglycans with a small amount of collagen. Due to these constituents, the nucleus pulposus has the capacity to bind water and usually contains 70-90 percent water by weight. Because of this high water content, the nucleus may be mechanically described as an incompressible hydrostatic material. The disc is under constant compressive forces even when the spine is not weight bearing as a result of the tension applied by the annulus fibrosus and the intervertebral ligaments.

The annulus fibrosus is a concentrically laminated structure which contains highly aligned collagen fibers and fibrocartilage embedded in amorphous ground substance. The annular layers are oriented at ±30 degrees to the longitudinal axis of the spine. In the inner laminae, these annular layers are anchored to the cartilaginous endplate while the outermost layer is attached directly into the osseous tissue of the vertebral body. Usually, the annulus fibrosus has approximately 8-12 layers and has an anterior portion which is about 1.2-1.5 times thicker than its posterior region. Mechanically, the annulus fibrosus is the main stabilizing structure which resists torsional and bending forces applied to the disc. A normal isolated disc provides approximately 35 percent of the torsional rigidity of a whole intervertebral joint.

The two vertebral endplates are composed of hyaline cartilage and separate the disc from the adjacent vertebral bodies. This layer acts as a transitional zone between the hard, bony vertebral bodies and the softer disc.

The spinal disc may be displaced or damaged due to trauma or a disease process. If this occurs, the nucleus pulposus may herniate and protrude into the vertebral canal or intervertebral foramen, in which case, it is known as a herniated or "slipped" disc. This disc may in turn press upon the spinal nerve that exits the vertebral canal through the partially obstructed foramen, causing pain or paralysis in the area of its distribution. The most frequent site of occurrence of a herniated disc is in the lower lumbar region. A disc herniation in this area often involves the inferior extremities by compressing the sciatic nerve. To alleviate this condition, it may be necessary to remove the involved disc surgically and fuse the two adjacent vertebrae. A number of procedures have been identified and are described in the orthopaedic literature. One such is described in "Orthopedics-Principles and Their Application", Samuel L. Turek, M.D., Lippincott Company, Third Edition, pp. 761-763. In this procedure, a hole is drilled in the spinal column straddling the damaged disc space and the two adjacent vertebral bodies. The hole is then filled with a cylindrical plug or dowel in order to fuse the vertebrae together. The fusion procedure is an excellent method of eliminating symptoms and yet maintaining joint stability, but at the expense of total loss of motion of the fused vertebral joint and increased stress in the juxta or adjacent segments. The adjacent discs will have increased motion and stress due to the increased stiffness of the fused segment. In the long term, this change in the mechanics of the motion of the spine causes these adjacent discs to degenerate. Obviously, a more desirable situation would involve replacing the damaged disc with a suitable biofunctional equivalent so as to return the patient's spine to normalcy. Heretofore, the development of a prosthetic joint device to replace the injured intervertebral disc has been unsuccessful due to the complexity of the structure and biomechanics of the normal disc. About 200,000 disc excision surgeries are performed in the United States each year.

Other spacers for spinal repair have been developed; see for instance those of U.S. Pat. No. 3,867,728, U.S. Pat. No. 4,309,777, U.S. Pat. No. 4,349,921, U.S. Pat. No. 4,554,273 and U.S. Pat. No. 4,714,469. None of these, however, have been commercially developed. The prostheses of U.S. Pat. Nos. 4,349,921, 4,553,273 and 4,714,469 are essentially rigid bodies which serve to stabilize the spine but do not allow motion within the disc itself. U.S. Pat. No. 4,309,777 consists of a disc which allows motion, but this is achieved by the use of springs contained within the body of the disc. This system suffers from the disadvantage of extreme complexity and doubtful long-term survival.

U.S. Pat. No. 3,867,728 by Stubstad et al. discloses a device which replaces the natural disc with one of similar shape and strength. The disc may be constructed from an elastic polymer such as silicone and reinforced with fabric. The top and bottom surfaces may be provided with an open pored material such as a velour to encourage tissue ingrowth. The purpose of this invention is to provide a system capable of withstanding the loads imposed upon it during normal human activities. As a result, the preferred construction of the disc provides for reinforcement against only compressional loads.

In practice, the spine is subjected to both compressional and torsional loading and, to be successful, any device must be capable of withstanding both forms. In addition to strength, any prosthetic disc must deform elastically in a similar manner to the natural structure in order that normal stresses are induced within the adjacent vertebral bodies. If too stiff a structure is used, then the disc will deform too little, and the natural discs both superior and inferior to the prosthetic device will be required to deform excessively. This is a similar situation to that which occurs when bony fusion across the disc is employed.

If, on the other hand, the device possesses too little stiffness, either in compression or torsion, then excessive motion will occur, the device will bulge out and pain may result. This is an equivalent situation to a failed bony fusion. U.S. Pat. No. 3,867,728 describes a device which is concerned only with the ultimate strength and not with any elastic properties. Therefore, the reinforcement of the elastomer through a fabric layer results only in an increase in compressional strength and fails to address the equally important problem of elasticity in compression and torsion. The fabric disclosed by U.S. Pat. No. 3,867,728 does not possess the necessary correct construction to provide the desired functional characteristics. As a result, the prosthesis of U.S. Pat. No. 3,867,728 fails to satisfy functional criteria for a replacement disc.

OBJECTS OF THE INVENTION

It is the object of the present invention to provide a novel intervertebral disc spacer which can be used to replace a damaged or diseased disc with a device that is chemically, geometrically and mechanically biocompatible and can be used to replace the natural structure.

It is a further object of this invention to provide a novel method of manufacturing a functional and biocompatible intervertebral disc spacer having similar or equivalent biomechanical properties to those of a normal disc.

It is a still further object of the present invention to provide a novel method of alleviating the pain and/or paralysis of a damaged or diseased disc which comprises replacing the damaged or diseased disc with a functional and biocompatible intervertebral disc spacer.

SUMMARY OF THE INVENTION

The present invention relates to a novel functional and biocompatible intervertebral disc spacer, its method of manufacture, and methods of use therefor. More particularly, the present invention concerns a functional and biocompatible intervertebral disc spacer having biomechanical properties similar or equivalent to those of a normal disc.

DETAILED DESCRIPTION OF THE INVENTION

Figure 1:
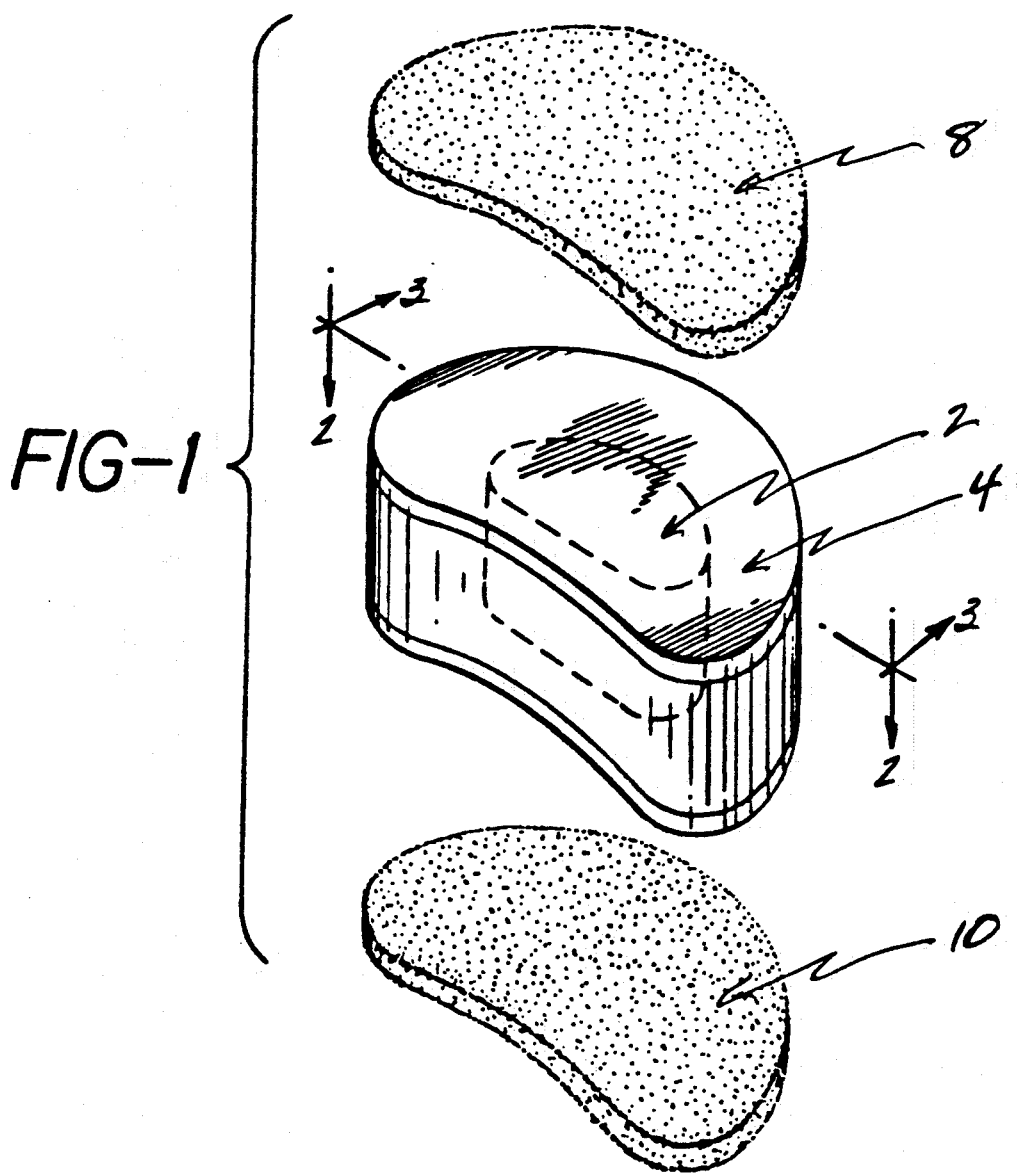
FIG. 1 is a view in perspective of a spinal disc spacer manufactured according to the present invention.
Figure 2:
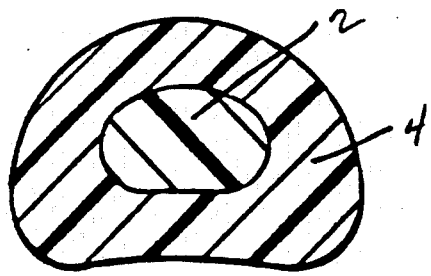
FIG. 2 is a top view of a spinal disc spacer manufactured according to the present invention.
Figure 3:
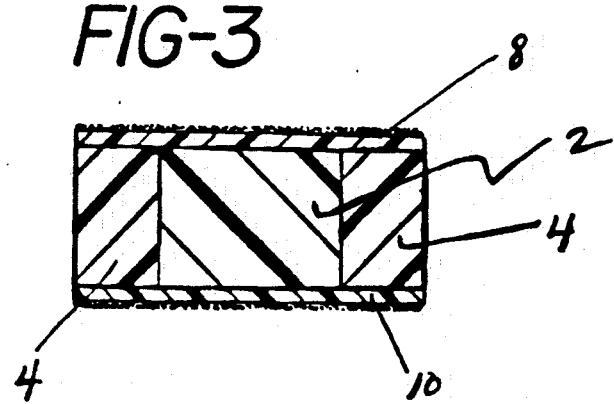
FIG. 3 is a cross-section view through the center of a spinal disc spacer manufactured according to the present invention.

The functional and biocompatible intervertebral spacer of the present invention comprises a central core 2 of a soft biocompatible elastomer shaped and sized so as to approximate the shape and size of a nucleus pulposus of a natural intervertebral disc; an outer ring 4 of stiffer elastomeric material surrounding said central core to approximate the size and shape of a natural annulus fibrosus; and endplates 8 and 10 comprised of a suitably stiff biocompatible material and affixed, one to each end, to the outer ring/central core. In a preferred embodiment, the core 2 will consist of 20-50% of the area of the spacer, and the outer ring 4 will consist of 50-80% of the area of the spacer. The relative size of the central core and the thickness of the outer ring in the radial direction, as well as the selection of material hardness, can be varied in order to more finely match the mechanical properties of the composite prosthesis to that of the normal disc.

The elastomeric material utilized in the core 2 and outer ring 4 is any appropriate biocompatible thermoplastic material. The hardness of the material for each component part of the prosthesis is chosen so that the composite prosthesis will reproduce the mechanical properties of the natural disc it is designed to replace. Preferably, the elastomeric material or materials utilized for the core 2 will have a hardness in the range of 20-70 shore-A. The elastomeric material or materials utilized for the outer ring 4 will preferably have hardnesses in the range of 40-80 shore-A. The outer ring 4 may be composed of one or as many as five layers of elastomers of varying hardness. Preferably, however, the outer ring 4 contains one or three layers of elastomers of varying hardness. The central core 2 may likewise contain 1-5 layers of elastomers of varying hardness, but 1-2 layers are preferred.

The biocompatible elastomeric material utilized in the present invention may be any suitable thermoplastic elastomeric material. Suitable thermoplastic elastomers are those commercially available under the trademark C-Flex ® (Concept, Inc.) or Pellethane ® (Dow Chemical). A preferred thermoplastic elastomer for use in the present invention is a biocompatible polysiloxane modified styrene-ethylene/butylene (SEBS) block copolymer sold by Concept Polymer Technologies, Inc., Clearwater, Fla., under the C-Flex ® trademark. These elastomers are available or can be formulated so as to form final products of varying stiffness. Although the present invention preferably utilizes the same elastomeric material in various degrees of stiffness for the various components of its disc spacer, it may also utilize different elastomeric materials for the various parts and various layers thereof.

In highly preferred embodiments of the present invention, the elastomeric material, relative areas and number of layers are chosen so as to afford a spacer having a mean axial stiffness of 1000-3500 newtons/mm and a mean torsional stiffness of 0.8-3.0 Nm/degree. Most preferably, a spacer will possess a mean axial stiffness of 2000-3000 newtons/mm and a mean torsional stiffness of 1-2 Nm/degree. These criteria afford a spacer with properties close to that of the human lumbar disc.

The endplates 8 and 10 for use in the spacer of the present invention can be manufactured from a variety of suitably stiff biocompatible materials; including more rigid elastomers of the same type as used in the disc itself. The suitably stiff endplate material must be relatively rigid and able to endure the biomechanical stresses placed upon it in the joint. Typically, the endplates are formed from rigid substances such as a biocompatible metal, for instance, precut titanium discs, and/or formed in a mold from biocompatible thermoplastic or thermoset resins, such as a polyurethane elastomer having a hardness of about 90-100 shore-A.

The endplates may also incorporate a mechanism for attachment to adjacent bony vertebral bodies. Such mechanisms include, but are not limited to, mechanical interlock, frictional fit, ingrowth into a porous structure such as a porous sintered surface, hydroxyapatite coatings or cementing agents such as polymethyl methylacrylate "bone cement."

The method of manufacture of the spacer of the present invention involves injection, transfer or compression molding of the core and outer wrapping.

Typical molding or casting techniques can be used to form polymer endplates. Metallurgical techniques can be used to form metal endplates. Both metal endplates and polymer endplates may have porous surfaces or hydroxyapatite surfaces to aid in attachment to adjacent bony vertebral bodies. These surfaces may be porous metallic or polymeric sintered surfaces, and would be used with bone cement.

The assembly of the spacer typically begins with the formation of a suitably shaped and sized core formed of the elastomer material. A preset amount of the powdered elastomer is compacted into a female mold of appropriate cross section and thickness. The filled mold with the male portion inserted is placed between thermal platens within a compression ram and then compressed. The pressure is then reduced. The temperature is increased until the melt temperature of the material is reached. The core may be held at an elevated temperature to facilitate bonding. This melt temperature is dependent upon the hardness and type of the chosen elastomeric material. The part is cooled to room temperature, and the nucleus is unmolded and any flash removed.

Next, the outer ring (annulus) is molded. The premolded nucleus is secured to the center of the bottom of the annular mold with a drop of adhesive. A preset amount of annular material, depending on the size of the annulus, is compacted by hand around the nucleus. Again, the male portion of the mold is positioned, and the pressure raised to approximately 1000 lbs. and then reduced and held at approximately 500 lbs. The temperature is then elevated to the temperature of the melting point of the annular material. The part may be held at an elevated temperature to facilitate bonding. The part is then cooled to room temperature, decompressed, unmolded and removed of any flash. If the outer ring (annulus) consists of more than one layer of elastomer, the varying layers of elastomers are molded to the core in a stepwise fashion, working from the core to the outer edge of the spacer.

The endplates 8 and 10 may be applied with additional elastomer to the top and bottom of the annulus/nucleus assembly. Alternatively, a preset amount of elastomeric endplate material can be placed on the bottom surface of the appropriate mold in a uniform layer. The annulus/nucleus is placed on top of the endplate material. Another uniform layer of material is placed on the top and compacted to form the second endplate. The male mold is positioned and the pressure and temperature cycles similar to that used for the previous molding steps is performed with the mold temperature raised to the temperature of the melting point of the endplate material. The part may be held at an elevated temperature to facilitate bonding. This type of assembly results in molded endplates.

Lastly, a porous layer of either hydroxylapatite or polymeric material can optionally be added to the outer surfaces of the endplates. The hydroxylapatite may be attached to the endplates by spreading a uniform layer of hydroxylapatite particles on a heated surface. The temperature of the particles is raised to the melt temperature of the endplate material and the flat surface of each endplate is pressed into the heated hydroxylapatite. A porous polymeric surface can be achieved by a process of sintering polymeric particulate to the surface or by including particles in the surface which are later dissolved in a separate process leaving behind controlled porosity.

Additionally, the endplates can be molded so as to provide for a mechanical interlock with the adjacent bone surface. They may also be subsequently "roughened" so as to provide a surface appropriate for attachment to the adjacent bones with polymethyl methacrylate bone cement.

Typically, molds are utilized to manufacture spacers having a geometry consistent with that of a natural disc. Although the disc size can, of course, be varied, a suitable size for the spacer is one having a cross section area of 1100 mm$^2$, a major diameter of 44 mm and a minor diameter of 30 mm.

The present invention contemplates manufacture of the spacers in a variety of sizes since one size is not suitable for all people or all locations within the spine. Additionally, the spacer of the present invention can be sized so that its total diameter is smaller than that of a natural disc, i.e., a size which approximates 30–80% of the diameter of the natural disc. This size of spacer can then be utilized in cases where only a central part of the natural disc is removed and replaced. In such cases, the damaged or diseased central portion is replaced by a spacer of approximately the same size as the portion removed. This type of replacement is particularly advantageous since the healthy portion of a patient's disc is retained. Obviously, molds can be developed for the various sizes necessary, and it is envisioned that the disc spacer of this invention will be manufactured in a variety of sizes so as to make the necessary selection available to the treating physician.

The following examples, and specifically Examples 1 and 2, illustrate the preparation and mechanical testing of a disc prosthesis of the present invention. Example 3 presents in vivo analysis of a prosthesis prepared with a hydroxylapatite coating thereon.

EXAMPLE 1

The assembly of the spacer begins with the formation of a suitably shaped and sized core formed of the elastomer material. A preset amount of the powdered elastomer is compacted into a female mold of appropriate cross section and thickness. The filled mold with the male portion inserted is placed between thermal platens within a compression ram. The mold is first compressed with an approximately 1000 lb. load. The pressure is then reduced and held at approximately 500 lbs. The temperature is increased at a rate of 5 degrees Celsius per minute until the melt temperature of the material is reached. The core may be held at an elevated temperature to facilitate bonding. This melt temperature is dependent upon the hardness and type of the chosen elastomeric material. The part is cooled to room temperature, and the nucleus is unmolded and any flash removed.

The outer ring (annulus) is molded next. The premolded nucleus is secured to the center of the bottom of the annular mold with a drop of adhesive. A preset amount of annular material, depending on the size of the annulus, is compacted by hand around the nucleus. Again, the male portion of the mold is positioned, and the pressure raised to approximately 1000 lbs. and then reduced and held at approximately 500 lbs. The temperature is then elevated at 5 deg. C./min. to the temperature of the melting point of the annular material. The part may be held at an elevated temperature to facilitate bonding. The part is then cooled to room temperature, decompressed, unmolded and removed of any flash.

If the endplates are separately manufactured, they are applied with additional elastomer to the top and bottom of the assembled annulus/nucleus. Alternately, the endplates may be directly molded onto the core-outer ring assembly. A preset amount of endplate material is placed on the bottom surface of the appropriate mold in a uniform layer. The annulus/nucleus is placed on top of the endplate material. Another uniform layer of material is placed on the top and compacted to form the second endplate. The male mold is positioned and the pressure and temperature cycles similar to that used for the previous molding steps is performed with the mold temperature raised to the temperature of the melting point of the endplate material. The part may be held at an elevated temperature to facilitate bonding.

Lastly, a porous layer of either hydroxylapatite or polymeric material can optionally be added to the outer surfaces of the endplates. The hydroxylapatite may be attached to the endplates by spreading a uniform layer of hydroxylapatite particles on a heated surface. The temperature of the particles is raised to the melt temperature of the endplate material and the flat surface of each endplate is pressed into the heated hydroxylapatite. A porous polymeric surface can be achieved by a process of sintering polymeric particulate to the surface or by including particles in the surface which are later dissolved in a separate process leaving behind controlled porosity.

EXAMPLE 2

Mechanical Testing

Both compression and torsion/compression tests were conducted. Many different compositions of prosthetic discs have been manufactured and mechanically tested. The devices tested in compression were axially loaded at a rate of 200 N/min. up to maximum load of 900N. Axial stiffness was measured between loads of 600 and 800N. The torsion/compression tests were conducted with an axial compression load of 800N and torqued at a rate of 2 Nm/s to a maximum rotation of 3 degrees. Torsional stiffness was measured between 1.5 and 2.5 degrees.

Single Component Discs

A series of discs were manufactured from single hardness compositions of C-Flex ®. The compressive and torsional properties of these discs are listed in Table I together with data from testing of human normal discs from the L4–L5 level.

TABLE I

| Mechanical Properties of Single Component Disc Prostheses | | |
|---|---|---|
| Disc Material | Mean Axial Stiffness (±SD) (N/mm) | Mean Torsional Stiffness (±SD) (Nm/deg) |
| 35A C-Flex ® | 387 (±3) | 0.16 (NA) |
| 50A C-Flex ® | 612 (±44) | 0.39 (NA) |
| 70A C-Flex ® | 1697 (±105) | 0.64 (NA) |
| 90A C-Flex ® | 3937 (±146) | 3.92 (NA) |
| HUMAN | 1328 (±241) | 2.06 (NA) |

NA = Not Available

These data serve to indicate that matching the combination of both compressive and torsional stiffnesses with a single grade of elastomer is not possible. If a hard grade of C-Flex ® such as 90A, is used, torsional properties may be matched but an excessively stiff system in compression is produced. Conversely, if a softer elastomer such as 70A is used, then the compressive stiffness is closer to that desired, however, the torsional stiffness is much lower.

Multi-Component Devices

In order to overcome the deficits outlined above, a series of prostheses were manufactured having compositions as listed in Table II. Their resultant compressive and torsional properties are listed in Table III.

TABLE II

| Disc Prosthesis Compositions | | | | |
|---|---|---|---|---|
| Disc Type | Nucleus Material | Nucleus Area | Annulus Material | Endplate Material |
| I | 35A C-Flex ® | 43% | 70A C-Flex ® | 90A C-Flex ® |
| II | 50A C-Flex ® | 43% | 70A C-Flex ® | 90A C-Flex ® |
| III | 35A C-Flex ® | 35% | 70A C-Flex ® | 90A C-Flex ® |
| IV | 35A C-Flex ® | 43% | 50A C-Flex ® | 90A C-Flex ® |

TABLE III

| Mechanical Properties of Multicomponent Disc Prostheses | | |
|---|---|---|
| Disc Type | Mean Axial Stiffness (±SD) (N/mm) | Mean Torsional Stiffness (±SD) (Nm/deg) |
| I | 1923 (±226) | 1.01 (±.06) |
| II | 2270 (±17) | 1.00 (±.07) |
| III | 2953 (±81) | 1.26 (±.04) |
| IV | 1008 (±55) | 0.40 (±.00) |
| HUMAN | 1328 (±241) | 2.06 (NA) |

NA = Not Available, Human Disc Level: (L4–L5)

The data show that by changing the various hardnesses and relative sizes of the annulus and nucleus that the mechanical properties of the disc prosthesis may be altered. The size and hardness of the nucleus dominate the properties in axial compression while the size and hardness of the annulus dominate the properties in torsion. In addition, the properties of the human normal disc are within range of the properties attainable with C-Flex ® for axial compression. The values for torsion appear low; however, in many cases at least 50% of natural annulus will remain in the patient after prosthetic disc insertion; further, the posterior bony elements of the spine will also remain intact. This remaining tissue will increase the overall in situ torsional properties to a normal level (see below).

Figure 4:
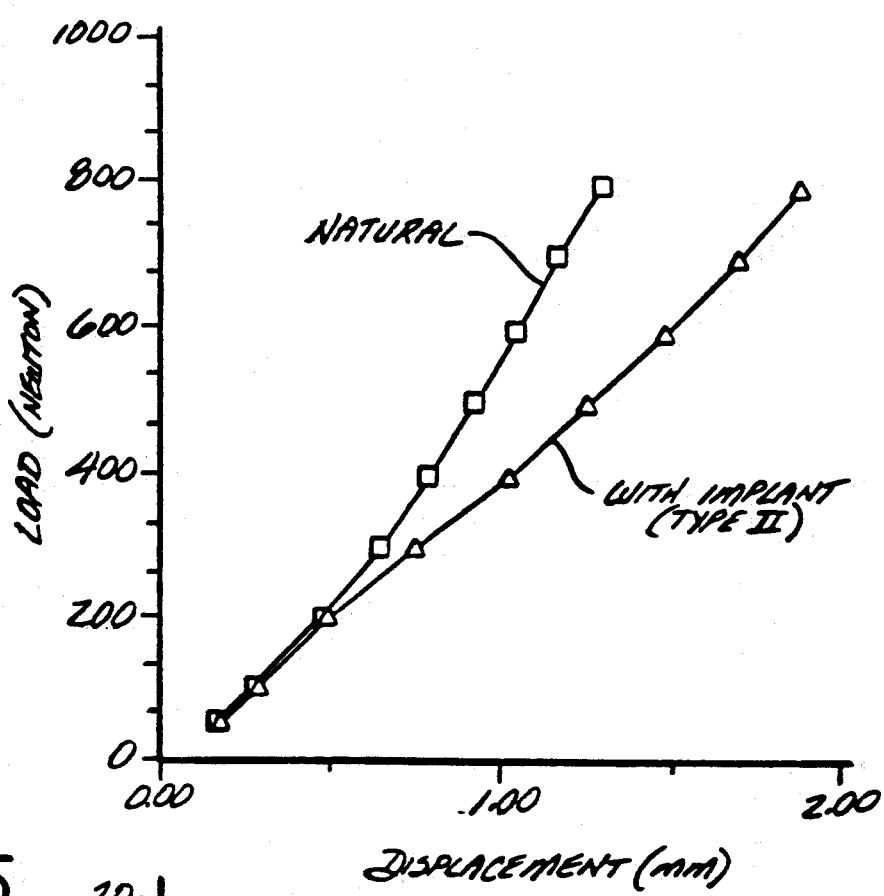
FIG. 4 is a graph showing the results of the mechanical behavior of a disc spacer produced according to the present invention compared to a natural disc in the axial compression test.
Figure 5:
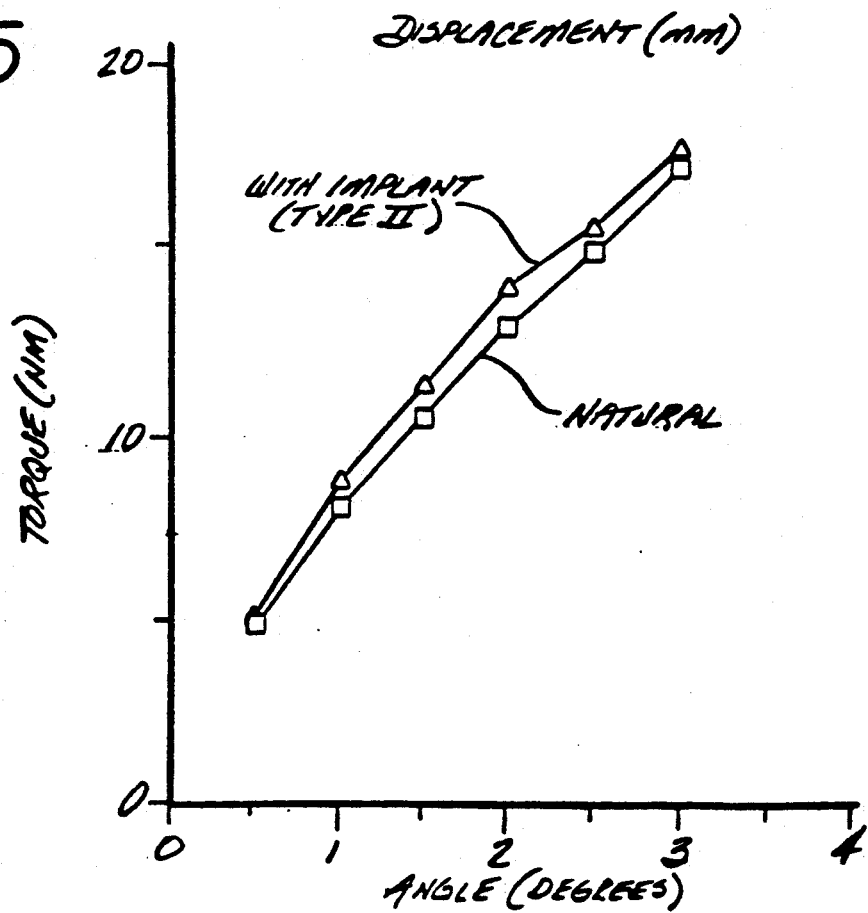
FIG. 5 is a graph showing the results of the mechanical behavior of a disc spacer produced according to the present invention compared to a natural disc in the compression torsion test.

Mechanical testing was also performed with the prosthesis implanted in the L4/L5 disc space of a functional spinal unit (two vertebral bodies with their common disc). A sample of the data in compression and torsion is shown in FIGS. 4 and 5. Each spinal unit was tested in both uniaxial compression and compression/torsion conditions in the intact state. The compression tests were performed in load control at a constant loading rate of 3.3 N/sec. The compression/torsion tests were conducted with the applied compression load held fixed at 800N while the rate of angular deflection was set to 0.1 degree/sec. Then these tests were repeated after the intervertebral disc prosthesis was implanted. Each prosthesis had also been tested alone.

EXAMPLE 3

In Vivo Analysis of Hydroxylapatite Coating

Animal experiments have been performed to demonstrate the benefit of using a porous material such as hydroxylapatite particulate to coat the surface of the endplates to enhance fixation of the prosthesis to bone. Small cylinders of thermoplastic C-Flex ® elastomer were manufactured and half were coated with hydroxylapatite in a manner similar to that of the disc prosthesis manufacturing process. These cylinders were implanted in the distal metaphyses of rabbit femora and examined at four and twelve weeks postoperatively. Five animals were utilized for each time period. Each rabbit received a coated sample in one femur while an uncoated sample was placed in the contralateral femur. Mechanical push-out tests were performed on four of the five animals in each time period and the remaining animal was used for histological examination.

The results from the mechanical testing revealed significantly higher shear strengths of the hydroxylapatite coated cylinders at both four and twelve weeks, indicating enhanced fixation and attachment over that of the uncoated polymeric cylinders. While the uncoated samples showed no increase in shear stress with time, the coated samples continued to increase in strength from four to twelve weeks. By twelve weeks, the coated implants had shear strengths five times that of the uncoated implants. Histologically, the coated implants revealed good apposition of the coating to the polymeric surface with partial wicking evident around the lateral surfaces of the particles. The hydroxylapatite surface was in intimate contact with trabecular bone with no evidence of fibrous tissue. Bony ingrowth into the interstices of the particulate hydroxylapatite was also observed. The uncoated implants demonstrated a fibrous tissue layer between the polymeric material and bone with a longitudinal orientation of the collagen bundles. No bony contact with the polymer was seen.

The disc spacer of the present invention thus provides a novel method of alleviating the pain and paralysis of a damaged or disease spine which comprises surgically replacing the damaged or diseased natural disc with one manufactured according to the present invention. Depending upon the patient's age and the position of the diseased or damaged disc, a physician will select a suitably sized replacement disc for insertion between the natural vertebrae.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A biocompatible intervertebral spacer comprising: a central core of an unreinforced soft biocompatible elastomeric material shaped and sized so as to approximate the shape and size of a nucleus pulposus of a natural intervertebral disc; an outer ring of stiff unreinforced elastomeric material surrounding said central core to approximate the size and shape of a natural annulus fibrous, said outer ring and said central core forming a disc having upper and lower surfaces; and endplates comprised of a stiff biocompatible material and affixed to each of said upper and lower surfaces with additional elastomeric material; said spacer having a mean torsional stiffness of from 0.8 Nm/degree to 3.0 Nm/degree and a mean axial stiffness of from 1000 newtons/mm to about 3000 newtons/mm.

2. A spacer according to claim 1 wherein the biocompatible elastomer is a thermoplastic polyurethane elastomer.

3. A spacer according to claim 1 wherein the biocompatible elastomer is a polysiloxane modified styrene-ethylene/butylene block copolymer.

4. A spacer according to claim 1 wherein the endplates contain hydroxylapatite.

5. A spacer according to claim 1 wherein the outer ring surrounding said central core contains 1-5 layers of a biocompatible elastomer of varying hardness.

6. A spacer according to claim 5 wherein the biocompatible elastomer is a thermoplastic polyurethane elastomer.

7. A spacer according to claim 5 wherein the biocompatible elastomer is a polysiloxane modified styrene-ethylene/butylene block copolymer.

8. A spacer according to claim 5 wherein the endplates contain hydroxylapatite.

9. A spacer according to claim 1 wherein the outer ring surrounding said central core contains 2-3 layers of a biocompatible elastomer of varying hardness.

10. A spacer according to claim 9 wherein the biocompatible elastomer is a thermoplastic polyurethane elastomer.

11. A spacer according to claim 9 wherein the biocompatible elastomer is a polysiloxane modified styrene-ethylene/butylene block copolymer.

12. A spacer according to claim 9 wherein the endplates contain hydroxylapatite.

13. A spacer according to claim 1 wherein the central core contains 1-5 layers of a biocompatible elastomeric material of varying hardness.

14. A spacer according to claim 13 wherein the biocompatible elastomer is a thermoplastic polyurethane elastomer.

15. A spacer according to claim 13 wherein the biocompatible elastomer is a polysiloxane modified styrene-ethylene/butylene block copolymer.

16. A spacer according to claim 13 wherein the endplates contain hydroxylapatite.

17. A spacer according to claim 1 wherein the endplates are metal.

18. A spacer according to claim 1 wherein the endplates have a porous metallic or polymeric sintered surface.

19. A spacer according to claim 1 wherein the endplates are further comprised of a means for mechanically interlocking with adjacent vertebrae during surgical implantation or use.

20. A spacer according to claim 1 wherein the end plates are provided with a roughened surface opposite the affixed surface thereby facilitating cementing the end plates to adjacent natural bone surfaces with polymethylmethacrylate bone cement.

21. A method of alleviating pain or paralysis caused by a damaged or diseased intervebral disc which comprises replacing all or part of the damaged or diseased disc with a biocompatible intervertebral spacer, said spacer comprising:
a central core of an unreinforced soft biocompatible elastomeric material shaped and sized so as to approximate the shape and size of a natural intervertebral disc;
an outer ring of stiff unreinforced elastomeric material surrounding said central core and approximating the size and shape of a natural annulus fibrousus, said outer ring and said central core forming a disc having upper and lower surface; and endplates comprised of a stiff biocompatible material and affixed to each of said upper and lower surfaces with additional elastomeric material;

said spacer having a mean torsional stiffness of from 0.8 Nm/degree to 3.0 Nm/degree and a mean axial stiffness of from 1000 newtons/mm to 3500 newtons/mm.

22. A method according to claim 21 wherein the core/outer ring of the disc spacer are comprised of a polysiloxane modified styrene-ethylene/butylene block copolymer.

23. A method according to claim 21 wherein the spacer contains metal endplates.

24. A method according to claim 21 wherein the spacer contains endplates of elastomeric material.

25. A method according to claim 21 wherein the endplates contain hydroxylapatite.

26. A spacer according to claim 21 wherein said mean torsional stiffness is from 1.0 Nm/degree to 2.0 Nm/degree and said mean axial stiffness is from 2000 newtons/mm to 3000 newtons/mm.

27. A biocompatible intervertebral disc spacer comprised of:

a central core comprised of an unreinforced, soft biocompatible elastomeric material shaped and sized to approximate the size and shape of a nucleus pulposus of a natural intervertebral disc;

an outer ring of stiff, unreinforced elastomeric material surrounding said central core which approximates the size and shape of a natural annulus fibrosus, said outer ring and central core forming a disc having upper and lower surfaces, and endplates comprised of a stiff biocompatible material and affixed to each of said upper and lower surfaces with additional elastomeric material, said spacer having a mean torsional stiffness of from 1.0 Nm/degree to 2.0 Nm/degree and a mean axial stiffness of from 2000 newtons/mm to 3000 newtons/mm.

28. In an implantable, biocompatible, intervertebral spacer which is comprised of (a) a central core having the softness of a natural nucleus pulposus, (b) an outer ring which angularly surrounds the central core and which is comprised of a biocompatible elastomeric material having the stiffness of a natural annulus fibrosus, said central core and outer ring forming a disc having upper and lower surfaces, and (c) upper and lower endplates affixed to the upper and lower surfaces of the disc respectively, each of such endplate being comprised of a biocompatible, stiff material affixed to the upper and lower surfaces of the disc, the improvement comprising utilizing an unreinforced material as the central core and annular outer ring which provides the spacer with a mean axial stiffness of about 1000–3000 newtons/mm and a mean torsional stiffness of about 0.8–3.0 Nm/degree.

* * * * *